United States Patent [19]  [11]  4,237,296
Gadient  [45]  Dec. 2, 1980

[54] QUATERNARY TROPANE ETHERS
[75] Inventor: Fulvio Gadient, Birsfelden, Switzerland
[73] Assignee: Sandoz Ltd., Basel, Switzerland
[21] Appl. No.: 7,229
[22] Filed: Jan. 29, 1979

Related U.S. Application Data
[63] Continuation of Ser. No. 810,496, Jun. 27, 1977, abandoned, which is a continuation of Ser. No. 652,808, Jan. 27, 1976, abandoned, which is a continuation of Ser. No. 452,978, Mar. 20, 1974, abandoned.

[30] Foreign Application Priority Data
Mar. 26, 1973 [CH] Switzerland ............... 4335/73

[51] Int. Cl.³ .................................. C07D 451/06
[52] U.S. Cl. ................................ 546/126; 424/265
[58] Field of Search ....................... 546/126; 424/265

[56] References Cited
U.S. PATENT DOCUMENTS
3,716,544  2/1973  Gadient .................... 546/126
3,725,415  4/1973  Boissier et al. ............ 546/126

FOREIGN PATENT DOCUMENTS
482719  1/1970  Switzerland ............... 546/126

Primary Examiner—Henry R. Jiles
Assistant Examiner—Richard A. Schwartz
Attorney, Agent, or Firm—Gerald D. Sharkin; Robert S. Honor

[57] ABSTRACT
The present invention concerns tropane derivatives of the formula

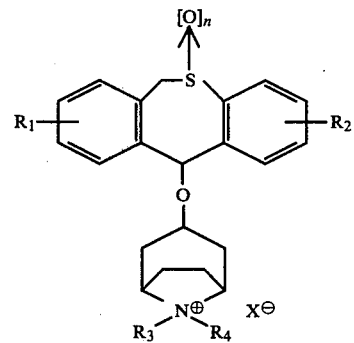

wherein
$R_1$ and $R_2$ are, independently, hydrogen, halogen, trifluoromethyl, lower alkyl or lower alkoxy,
$R_3$ and $R_4$ are, independently, lower alkyl, n is 0, 1 or 2, and p0 $X^{\ominus}$ is the anion of a pharmaceutically acceptable salt-forming acid.

1 Claim, No Drawings

QUATERNARY TROPANE ETHERS

This is a continuation, of application Ser. No. 810,496, filed June 27, 1977, now abandoned, which in turn is a continuation, of application Ser. No. 652,808, filed Jan. 27, 1976, now abandoned, which in turn is a continuation of Ser. No. 452,978, filed Mar. 20, 1974, now abandoned.

The present invention relates to new tropane derivatives.

In accordance with the invention there are provided new compounds of formula I,

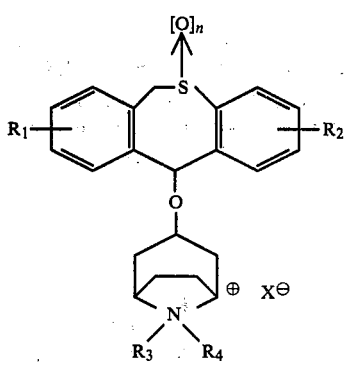

wherein $R_1$ and $R_2$ are, independently, hydrogen, halogen, trifluoromethyl, lower alkyl or lower alkoxy, $R_3$ and $R_4$ are, independently, lower alkyl, n is 0, 1 or 2, and $X^\ominus$ is the anion of a pharmaceutically acceptable salt-forming acid.

Halogen preferably signifies fluorine, chlorine or bromine; the lower alkyl or alkoxy group e.g. represented by $R_1$ or $R_2$ preferably has 1 to 4 carbon atoms.

The lower alkyl radical represented by the symbol $R_3$ or $R_4$ may, for example, be an alkyl radical of up to 4 carbon atoms; one of the radicals $R_3$ and $R_4$ preferably is methyl, the remaining radical is ethyl, isopropyl, n-butyl, and especially methyl or n-propyl.

Further, in accordance with the invention a compound of formula I may be obtained by a process comprising alkylating a compound of formula II,

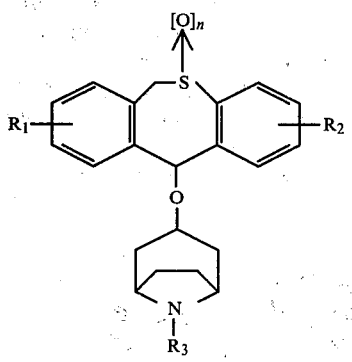

wherein $R_1$, $R_2$, $R_3$ and n are as defined above, with a compound of formula III, $$R_4-X^I \qquad \text{III}$$

wherein $R_4$ is as defined above, and $X^I$ is chlorine, bromine, iodine or lower alkyl-$SO_4$, and, if desired, effecting an anion exchange in the resulting compound of formula Ia,

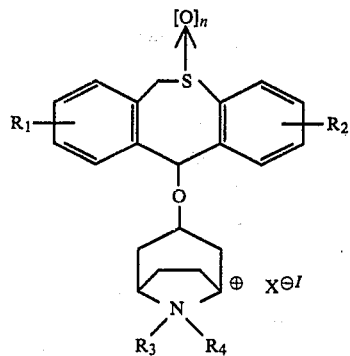

wherein $R_1$, $R_2$, $R_3$, $R_4$, n and $X^I$ are as defined above, to produce a compound of formula I.

The alkylation for the production of compounds of formula Ia may, for example, be effected as follows:

A compound of formula II, a 6,11-dihydrodibenzo[b-,e]thiepine derivative with a nortropan-3α-ol or nortropan-3β-ol radical, or the corresponding compound oxidized on the sulphur atom in the 5 position, may be dissolved in an inert organic solvent, and the corresponding compound of formula III, dissolved in the same solvent, may be added dropwise thereto.

The temperature range for the reaction with the alkylating agent $R_4$-$X^I$ preferably is from about 0° to 150° C. The reaction is preferably effected in a lower alcohol, e.g. ethanol, or acetone, conveniently at the boiling temperature. Alternatively it is possible to effect the reaction in the absence of a solvent, in an excess of alkylating agent, preferably at an elevated temperature.

It will be apparent that when $R_3$ is different from $R_4$ the resultant compound of formula I may exist in two isomeric forms due to the presence of an asymmetrically substituted nortropanyl nitrogen atom. In tropane chemistry it is believed that the electrophilic radical $R_4$ would attack the tropane nucleus of the compound of formula II substantially stereospecifically, along an equatorial (or axial) pathway. Accordingly by interchanging $R_3$ and $R_4$, e.g. methyl and propyl, on the starting materials of formulae II and III, different isomer forms of the compound of formula I may be obtained. In general introduction of a radical $R_4$ which is less bulky, e.g. methyl, than the radical $R_3$, e.g. other than methyl, present in the compound of formula II, is easier than the introduction of a radical $R_4$ which is more bulky than the radical $R_3$ present in the compound of formula II. For simplification products of the former introduction are referred to as the A series and products of the latter introduction as the B series.

The working up is effected in accordance with known methods. For example, the reaction solution may be diluted with a suitable solvent, whereby the compound of formula Ia crystallizes upon cooling.

If desired, the anion $X^{\ominus I}$ in the resulting compound of formula Ia may be exchanged for another anion $X^\ominus$, e.g. of a weak organic or inorganic acid, in known manner in accordance with the principles of a double reaction.

The compounds of formula II wherein $R_1$ and $R_2$ are hydrogen are known.

Compounds of formula IIa,

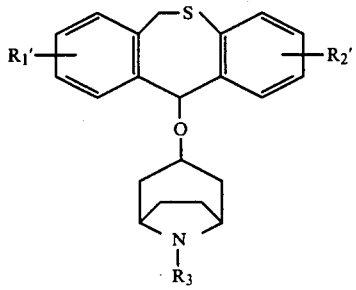

wherein
$R_1'$ and $R_2'$ are hydrogen, halogen, trifluoromethyl, lower alkyl or lower alkoxy, with the proviso that when one of $R_1'$ and $R_2'$ is hydrogen, the other of $R_1'$ and $R_2'$ is other than hydrogen, and
$R_3$ is as defined above,
may, for example, be obtained by reacting a compound of formula IV,

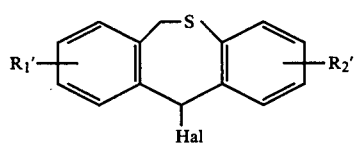

wherein
$R_1'$ and $R_2'$ are as defined above, and
Hal is chlorine, bromine or iodine,
with a compound of formula V,

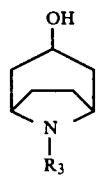

wherein $R_3$ is as defined above, in an inert organic solvent, e.g. an aromatic hydrocarbon such as benzene or xylene, preferably at an elevated temperature, e.g. at the boiling temperature of the reaction mixture.

The production of compounds of formula II oxidized on the sulphur atom in the 5 position and having substituted phenyl nuclei, may be effected with suitable oxidizing agents, using the quantity corresponding to the desired degree of oxidation. For example, the oxidized compounds may be obtained by (a) reacting a compound of formula IIa in a neutral or weakly acid solution with an alkali or alkaline earth metal salt of periodic acid, or with the stoichiometric amount of an organic peracid, or with the stoichiometric amount of hydrogen peroxide, to obtain a compound of formula IIb,

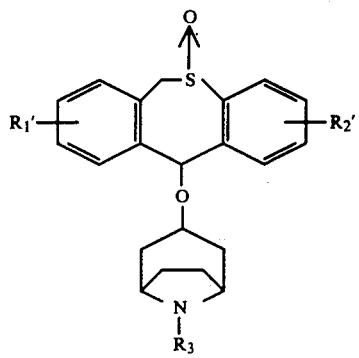

wherein $R_1'$, $R_2'$ and $R_3$ are as defined above, or (b) oxidizing a compound of formula IIa or IIb in acid solution with hydrogen peroxide or an organic peracid, to obtain a compound of formula IIc,

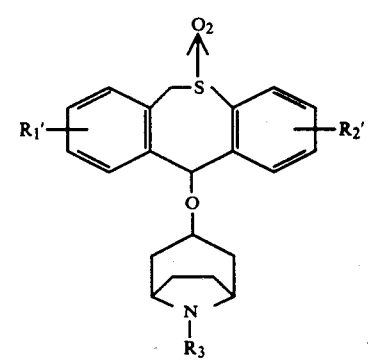

wherein $R_1'$, $R_2'$ and $R_3$ are as defined above.

The oxidation in accordance with process variant (a) is preferably effected at a lower temperature, especially between 0° and 50° C., and optionally in an inert solvent, e.g. acetic acid or acetone.

The oxidation in accordance with process variant (b) is preferably effected with an excess of hydrogen peroxide or an organic peracid and in an inert solvent, e.g. acetic acid or acetone, at an elevated temperature, preferably at a temperature between about 50° and 150° C.

The compounds used keep their steric configurations upon the oxidations in accordance with process variants (a) and (b).

If desired, the oxidation of the sulphur atom may alternatively be effected following the alkylation reaction on the nitrogen atom.

Compounds of formula IV may, for example, be produced by reducing a compound of formula VI,

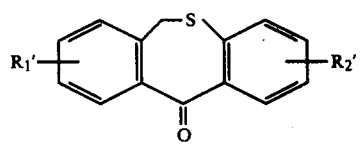

wherein $R_1'$ and $R_2'$ are as defined above, preferably with sodium borohydride, e.g. at 20° to 70° C., dissolving the resulting compound of formula VII,

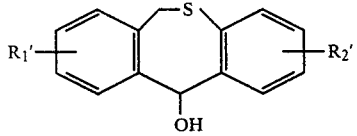

wherein R₁' and R₂' are as defined above, in a suitable anhydrous solvent, preferably an aromatic hydrocarbon such as benzene, and passing hydrogen chloride, hydrogen bromide or hydrogen iodide through the solution.

Insofar as the production of the starting materials is not described, these are known or may be produced in accordance with known processes, or in a manner analogous to the processes described herein or to known processes.

In the following non-limitative Examples all temperatures are indicated in degrees Centigrade.

EXAMPLE 1

6,11-dihydro-11-(3α-tropanyloxy)dibenzo[b,e]thiepine methiodide

A solution of 12.7 g of methyl iodide in 90 cc of ethanol is added dropwise to a solution of 21 g of 6,11-dihydro-11-(3α-tropanyloxy)dibenzo[b,e]thiepine in 150 cc of ethanol. The reaction mixture is heated at reflux for 1½ hours, is then diluted with 100 cc of methanol whilst hot, whereby the title compound crystallizes upon cooling. M.P. 170°–200° (decomp.).

EXAMPLE 2

6,11-dihydro-11-(3α-tropanyloxy)dibenzo[b,e]thiepine methobromide

The title compound is obtained by reacting 6,11-dihydro-11-(3α-tropanyloxy)dibenzo[b,e]thiepine with the corresponding amount of methyl bromide in a manner analogous to that described in Example 1. M.P. 218°–223°.

EXAMPLE 3

6,11-dihydro-11-(3α-tropanyloxy)dibenzo[b,e]thiepine-5-oxide methiodide

The title compound is obtained by reacting 6,11-dihydro-11-(3α-tropanyloxy)dibenzo[b,e]thiepine-5-oxide with methyl iodide in a manner analogous to that described in Example 1. M.P. 270°–275°.

EXAMPLE 4

6,11-dihydro-11-(3α-tropanyloxy)dibenzo[b,e]thiepine-5,5-dioxide methiodide

The title compound is obtained by reacting 6,11-dihydro-11-(3α-tropanyloxy)dibenzo[b,e]thiepine-5,5-dioxide with methyl iodide in a manner analogous to that described in Example 1. M.P. 335°–340° (decomp.).

EXAMPLE 5

6,11-dihydro-11-(3α-tropanyloxy)dibenzo[b,e]thiepine-5,5-dioxide methobromide

The title compound is obtained by reacting 6,11-dihydro-11-(3α-tropanyloxy)dibenzo[b,e]thiepine-5,5-dioxide with the corresponding amount of methyl bromide in a manner analogous to that described in Example 1. M.P. 335°–340° (decomp.).

EXAMPLE 6

6,11-dihydro-11-(3α-tropanyloxy)dibenzo[b,e]thiepine-5-oxide methobromide

A solution of 8.5 g of methyl bromide in 70 cc of ethanol is added dropwise to a solution of 21.7 g of 6,11-dihydro-11-(3α-tropanyloxy)dibenzo[b,e]thiepine-5-oxide in 150 cc of ethanol. The reaction mixture is then allowed to stand at room temperature for 18 hours. After concentrating the ethanolic solution working up is effected by taking up the oily residue in acetone, whereby the title compound crystallizes. M.P. 195°–198°.

EXAMPLE 7

11-(8-ethyl-3α-nortropanyloxy)-6,11-dihydrodibenzo[b,e]thiepine methobromide 13 g of a 40% solution of methyl bromide in ethanol are added to a solution of 4 g of 11-(8-ethyl-3α-nortropanyloxy)-6,11-dihydrodibenzo[b,e]thiepine in 30 cc of ethanol and the reaction mixture is allowed to stand in a refrigerator at 2° for 48 hours. The reaction mixture is subsequently concentrated completely at reduced pressure and the residue is taken up in acetone, whereby the title compound crystallizes. M.P. 160°.

EXAMPLE 8

6,11-dihydro-11-(8-n-propyl-3α-nortropanyloxy)dibenzo[b,e]thiepine methobromide, isomer of the A series The title compound is obtained from 6,11-dihydro-11-(8-n-propyl-3α-nortropanyloxy)dibenzo[b,e]thiepine in a manner analogous to that described in Example 7. M.P. 205°–206° (from acetone).

EXAMPLE 9

6,11-dihydro-11-(8-isopropyl-3α-nortropanyloxy)-dibenzo[b,e]thiepine methobromide The title compound is obtained in a manner analogous to that described in Example 7, from 6,11-dihydro-11-(8-isopropyl-3α-nortropanyloxy)dibenzo[b,e]thiepine after allowing to stand for 72 hours with a solution of methyl bromide in ethanol at 2° to 4°. M.P. 258°–260° (from ethanol/ether).

EXAMPLE 10

2-chloro-6,11-dihydro-11-(3α-tropanyloxy)dibenzo[b,e]thiepine methobromide

The title compound is obtained in a manner analogous to that described in Example 9, from 2-chloro-6,11-dihydro-11-(3α-tropanyloxy)dibenzo[b,e]thiepine. M.P. 190°–192° (from acetone).

The 2-chloro-6,11-dihydro-11-(3α-tropanyloxy)-dibenzo[b,e]thiepine, used as starting material, may, for example, be produced as follows:

(a) A mixture of 26 g of 2-chloro-6,11-dihydrodibenzo[b,e]thiepin-11-one and 7.6 g of sodium borohydride in 250 cc of ethanol is stirred for 1½ hours at 65° and subsequently for one hour at room temperature. The reaction mixture is then poured on one liter of water, is extracted with chloroform, the chloroform extracts are washed with water and dried with sodium sulphate. After concentrating the chloroform phase, dilution is effected with ether, whereby 2-chloro-6,11-dihydrodibenzo[b,e]thiepin-11-ol crystallizes. M.P. 160°–162°.

(b) Hydrogen chloride gas is passed through 8 g of 2-chloro-6,11-dihydrodibenzo[b,e]thiepin-11-ol in 60 cc of absolute benzene for 10 minutes while cooling. 3.7 g of calcium chloride are subsequently added, filtration is effected after 5 minutes and the solvent is removed at reduced pressure. The residue is dissolved in 50 cc of absolute xylene and added dropwise to a boiling solution of 4.3 g of tropine in 40 cc of absolute xylene. The reaction mixture is subsequently heated at reflux for one hour, is cooled to room temperature, is diluted with 50 cc of ether and extracted with 2 normal hydrochloric acid. After washing the acid extract with ether, it is rendered alkaline with a caustic soda solution while cooling and the aqueous phase is extracted with ether. The organic phase is washed with water, dried over sodium sulphate, and the solvent is removed, whereby 2-chloro-6,11-dihydro-11-(3α-tropanyloxy)dibenzo[b,e]thiepine is obtained as an oil, which is used for the next stage without further purification. $R_f$ value 0.7 (adsorbent: silica gel; eluant: chloroform/ethanol/conc. ammonia 90:10:2).

EXAMPLE 11

6,11-dihydro-2-methoxy-11-(3α-tropanyloxy)dibenzo[b,e]thiepine methobromide 5.2 g of methyl bromide are added to a solution of 4 g of 6,11-dihydro-2-methoxy-11-(3α-tropanyloxy)-dibenzo[b,e]thiepine in 50 cc of ethanol and the reaction mixture is allowed to stand in a refrigerator for 16 hours. The reaction mixture is then completely concentrated at reduced pressure and the residue is dissolved in 30 cc of ethanol, whereby the title compound crystallizes. M.P. 175°–177°.

The 6,11-dihydro-2-methoxy-11-(3α-tropanyloxy)-dibenzo[b,e]thiepine, used as starting material, may, for example, be produced as follows:
(a) 6,11-dihydro-2-methoxy-dibenzo[b,e]thiepin-11-ol is produced from 6,11-dihydro-2-methoxy-dibenzo[b,e]thiepin-11-one and sodium borohydride in a manner analogous to that described in Example 10, stage (a). M.P. 142°–144° (from ether/pentane).
(b) 6,11-dihydro-2-methoxy-dibenzo[b,e]thiepin-11-ol is activated and reacted with tropine in a manner analogous to that described in Example 10, stage (b), whereby 6,11-dihydro-2-methoxy-11-(3α-tropanyloxy)dibenzo[b,e]thiepine is obtained as an oil which is used in the next stage without further purification.
$R_f$ value 0.65 (adsorbent: silica gel; eluant: chloroform/ethanol/conc. ammonia 90:10:2).

EXAMPLE 12

6,11-dihydro-11-(8-n-propyl-3α-nortropanyloxy)dibenzo[b,e]thiepine methobromide, isomer of the B series 7 g of 6,11-dihydro-11-(3α-tropanyloxy)dibenzo[b,e]thiepine are dissolved in 25 cc of n-propyl bromide and the solution is heated in an oil bath of 90° for 12 hours. After cooling, the crystalline precipitate is filtered off, is washed well with ether and dried. The title compound, having a M.P. of 160°, is obtained.

EXAMPLE 13

11-(8-n-butyl-3α-nortropanyloxy)-6,11-dihydrodibenzo[b,e]thiepine methobromide 12 g of a 40% solution of methyl bromide in ethanol are added to a solution of 3.7 g of 11-(8-n-butyl-3α-nortropanyloxy)-6,11-dihydrodibenzo[b,e]thiepine in 40 cc of ethanol and the reaction mixture is allowed to stand in a refrigerator at 2° for 72 hours. The reaction mixture is then completely concentrated at reduced pressure and the residue is taken up in ethyl acetate, whereby the title compound crystallizes. M.P. 140°.

In a manner analogous to that described in Example 1, the following compounds of formula I are obtained, wherein n is 0, $R_3$ and $R_4$ are both methyl and having the 3β configuration.

|     | $R_1$    | $R_2$   | X         |
|-----|----------|---------|-----------|
| (a) | 7-Cl     | 1-F     | $CH_3SO_4$ |
| (b) | 8-$CF_3$ | 2-$CF_3$ | Cl        |
| (c) | 9-$CH_3$ | 3-$CH_3$ | $CH_3SO_4$ |
| (d) | 10-$CH_3O$ | 4-Br  | Br        |

The compounds of formula I have not been described in the literature.

The compounds of formula I are useful because they possess pharmacological activity in animals. In particular, the compounds of formula I are useful as bronchospasmolytic agents, as indicated in standard tests, e.g. the Konzett-Rössler test, by an inhibition of the bronchospasms induced by histamine in cats on i.v. administration of from 0.03 to 0.1 mg/kg animal body weight of the compounds, by acetylcholine in cats on i.v. administration of from 0.01 to 1.0 mg/kg animal body weight of the compounds, and by acetylcholine in conscious guinea pigs on s.c. administration of from 0.05 to 0.1 mg/kg animal body weight of the compounds.

For the above mentioned use the dosage will, of course, vary depending on the compound employed, mode of administration and therapy desired. However, in general, satisfactory results are obtained when administered at a daily dosage of from 0.01 mg to about 1 mg per kg animal body weight, conveniently given in divided doses 2 to 4 times a day or in sustained release form. For the larger mammal, the total daily dosage is in the range from about 1 to about 5 mg, and dosage forms suitable for oral administration comprise from about 0.3 mg to about 2.5 mg of the compounds admixed with a solid or liquid pharmaceutical carrier or diluent.

Representative salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in association with a pharmaceutical carrier or diluent. Such compositions conveniently contain about or more than 1% by weight of the compound of formula I and may be prepared by conventional techniques to be in conventional forms, for example, capsules, tablets, suppositories, dispersible powders, syrups, elixirs, aerosols, suspensions or solutions, for per oral, e.g. by inhalation, enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets, and aerosol forms.

Compositions for inhalation therapy may be prepared in conventional manner, e.g. in the form of nebulizers, vaporizers and aerosols. Unit doses may be provided by a metered value system. Such compositions are especially useful for the bronchospasmolytic use of the compounds. Propellants that may be used in such compositions include fluorinated hydrocarbons.

I claim:
1. A compound selected from the group consisting of 6,11-dihydro-2-methoxy-11-(3-tropanyloxy)-dibenzo[b,e]thiepine methobromide; 2-chloro-6,11-dihydro-11-(3-tropanyloxy)-dibenzo[b,e]thiepine methobromide; and 11-(8-ethyl-3-nortropanyloxy)-6,11-dihydrodibenzo[b,e]thiepine methobromide.

* * * * *